(12) United States Patent
Kellomaki et al.

(10) Patent No.: US 9,816,906 B2
(45) Date of Patent: Nov. 14, 2017

(54) APPARATUS AND METHOD FOR STRETCH MEASUREMENTS OF TISSUE WEBS

(71) Applicant: Honeywell International Inc., Morristown, NJ (US)

(72) Inventors: Markku Kellomaki, Pohjois-Savo (FI); Antti Paavola, Tampere (FI)

(73) Assignee: Honeywell International Inc., Morris Plains, NJ (US)

( * ) Notice: Subject to any disclaimer, the term of this patent is extended or adjusted under 35 U.S.C. 154(b) by 277 days.

(21) Appl. No.: 14/549,139

(22) Filed: Nov. 20, 2014

(65) Prior Publication Data
US 2015/0308934 A1 Oct. 29, 2015

Related U.S. Application Data

(60) Provisional application No. 61/984,147, filed on Apr. 25, 2014.

(51) Int. Cl.
*G01N 33/34* (2006.01)
*G01N 3/08* (2006.01)
*D21G 9/00* (2006.01)
*G01B 11/245* (2006.01)

(52) U.S. Cl.
CPC .............. *G01N 3/08* (2013.01); *D21G 9/0009* (2013.01); *G01B 11/245* (2013.01); *G01N 33/346* (2013.01); *G01N 2203/0282* (2013.01)

(58) Field of Classification Search
CPC ................................ G01N 3/08; G01N 33/346
USPC ............................................................ 73/826
See application file for complete search history.

(56) References Cited

U.S. PATENT DOCUMENTS

| | | | |
|---|---|---|---|
| 3,838,596 A | 10/1974 | Neuenschwander | |
| 3,905,533 A | 9/1975 | Corse | |
| 4,350,275 A * | 9/1982 | Kuhn | B65H 23/042 |
| | | | 226/104 |
| 5,013,403 A | 5/1991 | Chase | |
| 5,182,722 A | 1/1993 | Hain | |

(Continued)

FOREIGN PATENT DOCUMENTS

WO    WO 87/03087    5/1987

OTHER PUBLICATIONS

Extended European Search Report dated Sep. 16, 2015 in connection with European Patent Application No. 15163076.1; 5 pages.

(Continued)

*Primary Examiner* — Walter L Lindsay, Jr.
*Assistant Examiner* — Philip Marcus T Fadul (57) ABSTRACT

A method includes, using at least one processing device, obtaining position measurements and/or tilt angle measurements associated with a tissue web and identifying a stretch measurement associated with the tissue web using the obtained measurements. Identifying the stretch measurement could include using one or more mathematical formulas to calculate the stretch measurement associated with the tissue web using the obtained measurements. The one or more mathematical formulas could be defined using laboratory stretch values of multiple training webs. Different mathematical formulas can be associated with training webs having different characteristics, and the method may further include selecting at least one of the mathematical formulas based on one or more characteristics of the tissue web.

24 Claims, 6 Drawing Sheets

(56) References Cited

U.S. PATENT DOCUMENTS

| | | | |
|---|---|---|---|
| 5,298,121 | A | 3/1994 | Kilmister |
| 5,384,080 | A * | 1/1995 | Feistkorn ............ B29C 55/065 |
| | | | 264/289.6 |
| 5,485,386 | A | 1/1996 | Andreasson |
| 5,628,227 | A | 5/1997 | LaPlante |
| 6,250,146 | B1 | 6/2001 | Callendrier |
| 6,363,621 | B1 | 4/2002 | James, Jr. et al. |
| 6,517,679 | B1 * | 2/2003 | Mustonen ............ D21G 9/0027 |
| | | | 162/198 |
| 6,752,013 | B2 | 6/2004 | Cote et al. |
| 6,985,789 | B2 | 1/2006 | Carlson et al. |
| 6,993,964 | B2 | 2/2006 | Franz et al. |
| 7,001,485 | B2 | 2/2006 | Koivukunnas et al. |
| 7,423,754 | B2 | 9/2008 | Wysokowski et al. |
| 7,647,845 | B2 | 1/2010 | Hiesinger |
| 7,780,817 | B2 * | 8/2010 | Hellstrom ............ D21G 9/0036 |
| | | | 162/198 |

OTHER PUBLICATIONS

"ISO 12625-4: Tissue Paper and Tissue Products—Part 4: Determination of Tensile Strength, Stretch at Break and Tensile Energy Absorption"; Int'l Standard ISO; Apr. 15, 2005; 14 pages.

Parent, et al.; "Measurement and Correction of Baggy Edges on Paper Machines"; TAPPI; PaperCon 2011; May 1-4, 2011; 28 pages.

Valenzuela, et al.; "Sensorless Tension Control in Paper Machines"; IEEE Transactions on Industry Applications vol. 39, No. 2; Mar./Apr. 2003; 11 pages.

"Honeywell Introduces Sensor to Improve Paper and Board Printability and Increase Customer Satisfaction"; www.honeywellprocess.com/en-US/news-and-events; Jun. 2, 2010; 1 page.

"Tissue Paper and Tissue Products—Part 4: Determination of Tensile Strength, Stretch at Break and Tensile Energy Absorption"; ISO 12625-4:2005; Instron.com; 1 page.

European Patent Office, "Communication pursuant to Article 94(3) EPC ," Application No. 15 163 076.1-1559, Oct. 11, 2016, 3 pages, publisher European Patent Office, Rijswijk Netherlands.

"Tissue Paper and Tissue Products—Part 4: Determination of Tensile Strength, Stretch at Break and Tensile Energy Absorption", ISO International Standard, ISO 12625-4, First Edition, Apr. 15, 2005, 14 pages.

European Office Action in European Patent Application No. EP 15 163 076.1, dated May 12, 2017, 4 pages.

\* cited by examiner

APPARATUS AND METHOD FOR STRETCH MEASUREMENTS OF TISSUE WEBS

CROSS-REFERENCE TO RELATED APPLICATION AND PRIORITY CLAIM

This application claims priority under 35 U.S.C. §119(e) to U.S. Provisional Patent Application No. 61/984,147 filed on Apr. 25, 2014. This provisional patent application is hereby incorporated by reference in its entirety.

TECHNICAL FIELD

This disclosure relates generally to measurement systems. More specifically, this disclosure relates to an apparatus and method for stretch measurements of tissue webs.

BACKGROUND

Various manufacturers operate systems that produce or process tissue paper (also called tissue webs). This includes systems that produce or process creped tissue paper, which represents tissue paper that has been "creped" or crinkled. Tissue paper can have various properties that are important to downstream processes and end users.

SUMMARY

This disclosure provides an apparatus and method for stretch measurements of tissue webs.

In a first embodiment, a method includes, using at least one processing device, obtaining position measurements and/or tilt angle measurements associated with a tissue web and identifying a stretch measurement associated with the tissue web using the obtained measurements.

In a second embodiment, a non-transitory computer readable medium embodies a computer program. The computer program includes computer readable program code for obtaining position measurements and/or tilt angle measurements associated with a tissue web. The computer program also includes computer readable program code for identifying a stretch measurement associated with the tissue web using the obtained measurements.

In a third embodiment, an apparatus includes at least one memory configured to store position measurements and/or tilt angle measurements associated with a tissue web. The apparatus also includes at least one processing device configured to identify a stretch measurement associated with the tissue web using the obtained measurements.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which:

FIGS. 9 through 10B illustrate example techniques for identifying crepe structures of tissue webs according to this disclosure.

DETAILED DESCRIPTION

FIGS. 1 through 10B, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Tissue webs can have various properties that are important to downstream processes and end users. One example is the web's "stretch" property, which represents a measure of the amount that a web can potentially stretch before breaking. A stable stretch property is often a desired or needed property in a tissue web since it can affect various processing operations that occur using the tissue web. For example, a web with a higher stretch property may be desired because the web can be elongated more before it breaks compared to a web with a lower stretch property. As another example, a web with a low variation in its stretch property may be desired because it helps in converting operations and general "runnability" of the web. Rewinding, embossing, printing, trimming, cutting, and packaging operations tend to elongate a tissue web. A tissue web typically elongates very easily due to its low tensile stiffness. Elongation of a tissue web is mostly plastic and not elastic, meaning the tissue web tends to remain elongated and not return to its pre-elongated shape. Various processes, such as those described above, often need to be adjusted in order to reduce the likelihood of a tissue web folding or breaking. However, this is difficult to accomplish if the stretch property of the web varies too much.

In conventional systems, a laboratory test of a tissue web's stretch property is performed after the tissue web is manufactured or processed and collected at a reel. For example, in accordance with the International Organization for Standardization (ISO) 12625-4:2005 specification, a laboratory stretch measurement of a sample can be determined as the elongation percentage at which the sample breaks under tension. Obviously, the approach described in the 12625-4:2005 specification is destructive and cannot be used online in a production or processing environment. As a result, this approach does not allow efficient process adjustments to be made to maintain acceptable stretch during manufacturing or processing of the tissue web. In some cases, an entire reel of manufactured or processed tissue paper may need to be rejected, which leads to monetary and production losses.

Figure 1:
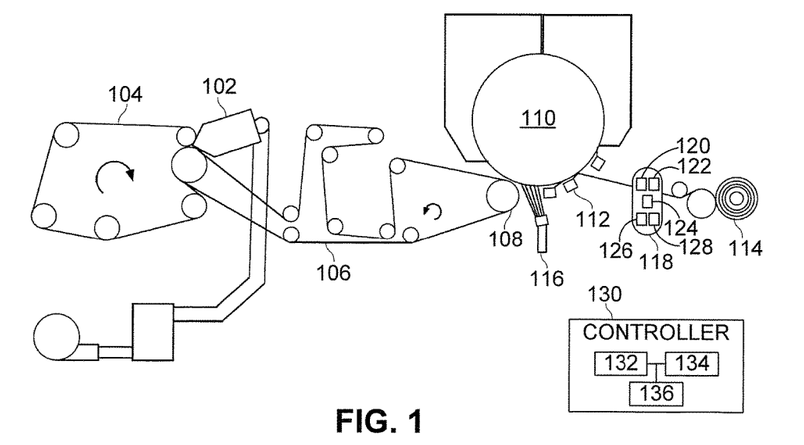
FIG. 1 illustrates an example system for identifying stretch measurements of a tissue web according to this disclosure.

FIG. 1 illustrates an example system 100 for identifying stretch measurements of a tissue web according to this disclosure. As shown in FIG. 1, an aqueous slurry of paper fibers is provided to a headbox 102. The headbox 102 deposits the slurry onto a substrate 104, such as a wire mesh. The substrate 104 allows water from the slurry to drain away and leave a wet web of paper fibers on the substrate 104. The substrate 104 is moved along its length in a continuous loop by multiple rollers.

The wet web of paper fibers is transferred from the substrate 104 to a press felt 106. The press felt 106 is also moved along its length in a continuous loop by multiple rollers. The press felt 106 carries the wet web of paper fibers to a pressure roll 108. The pressure roll 108 transfers the wet web of paper fibers to the surface of a Yankee dryer 110 (also called a creping cylinder). The Yankee dryer 110 dries the web of paper fibers as the Yankee dryer 110 rotates.

The dried web of paper fibers is removed from the surface of the Yankee dryer 110 by the application of a creping doctor 112. The creping doctor 112 includes a blade that forms crepe structures in the web of paper fibers. The resulting creped web of paper fibers is collected on a reel or drum 114 as a creped tissue web.

A spray boom 116 sprays material, such as a sizing agent, onto the Yankee dryer 110 before the wet web of paper fibers contacts the Yankee dryer 110. The sizing agent helps to hold the wet web of paper fibers against the Yankee dryer 110. The amount of creping produced by the creping doctor 112 depends in part on the amount of sizing agent applied to the Yankee dryer 110 by the spray boom 116. In some embodiments, the spray boom 116 includes multiple nozzles arranged across the width of the Yankee dryer 110, where each nozzle sprays the sizing agent onto a portion or zone of the Yankee dryer 110. The nozzles can have associated actuators that are controlled in order to control the amount of sizing agent sprayed onto the Yankee dryer 110.

As noted above, the tissue paper industry lacks online (non-laboratory) methods and devices for measuring and controlling the stretch property of tissue webs. In accordance with this disclosure, a scanner 118 includes one or more sensors used to measure the stretch property of a tissue web. For example, the scanner 118 could characterize the vertical position and/or tilt angle of the tissue web, such as by measuring the distance from the web to a sensor (or other known location) or by measuring the tilt angle of the web with respect to a sensor (or other known location). This could be done in an "open draw," meaning an area where the web is not supported and can sag (such as under its own weight). In this example, the open draw occurs after the Yankee dryer 110, although any other open draw could be used.

The measurements characterizing the vertical position and/or tilt angle of the tissue web are used to predict the stretch property of the tissue web. For example, measurements characterizing vertical position and/or tilt angle of the tissue web could be inserted into one or more mathematical formulas to calculate stretch values. As another example, measurements characterizing vertical position and/or tilt angle of the tissue web could be correlated with vertical position and/or tilt angle measurements associated with laboratory measurements of known stretch values to estimate the stretch property of the web that is currently being manufactured or processed.

Note that the measurements characterizing the vertical position and/or tilt angle of the tissue web could represent any suitable values. For example, the measurements could include pointwise position measurements, multi-point position measurements in the machine direction (MD), multi-point position measurements in the cross direction (CD), multi-point position measurements in both directions, or local tilt angle measurements of the web in any suitable direction(s) (including the machine direction and/or the cross direction). The machine direction refers to the direction along the (longer) length of the web, while the cross direction refers to the direction along the (shorter) width of the web. The measurements characterizing the vertical position and/or tilt angle of the tissue web could also represent single values or statistical or other parameters extracted from or based on measurement values, profiles, or fields.

The measurements characterizing the vertical position and/or tilt angle of the tissue web could further represent discrete or continuous (non-discrete) measurements taken in any suitable direction(s) of the web.

Also note that while the use of a scanner 118 with moving sensors may be described, measurements characterizing the vertical position and/or tilt angle of a tissue web could be generated using any suitable moving or fixed sensors. Each sensor in the scanner 118 could be stationary or move across part or all of the width of the tissue paper being manufactured or processed. There could be a single fixed sensor, multiple fixed sensors, a single moving sensor, multiple moving sensors, or a combination of fixed and moving sensors.

The scanner 118 includes any suitable structure(s) for measuring one or more characteristics of a tissue web, including its stretch property. For example, in some embodiments, the scanner 118 could include a signal generator 120 and a signal receiver 122. The signal generator 120 generates a signal that interacts with the web, and the signal receiver 122 receives the signal that has interacted with the web. The scanner 118 could also include at least one processing device 124 that analyzes data from the signal receiver 122 to identify one or more characteristics of the tissue web. For instance, the processing device 124 could analyze images to identify the position and/or tilt of the web (where the position could be expressed as a distance from the sensor). The processing device 124 could then correlate the position and/or tilt measurements with known stretch values to estimate the stretch property of the current web being measured. In addition, the scanner 118 could include at least one memory 126 storing instructions and data used, generated, or collected by the scanner 118 and at least one interface 128 facilitating communication with other devices, such as a process controller.

The scanner 118 could support any suitable technique for identifying distance/tilt measurements associated with a web in order to identify stretch measurements of the web. The technique used can determine what type of signal generator 120 and signal receiver 122 are used in the scanner 118 and what type of processing occurs in the processing device 124. Example techniques could include the use of optical triangulation gauges (such as laser triangulation gauges), proximity sensors (such as capacitive or ultrasound sensors), structured light and camera sensors, stereographic techniques, interferometric techniques, Moiré fringe and other interference techniques, laser speckle techniques, and contacting techniques. When structured light and camera sensors are used, one or more patterns (such as spots, lines, grids, images, or random dots) could be projected onto the web, and an image of the one or more projected patterns can be captured using a camera and analyzed. When a Moiré fringe or other interference technique is used, a two-dimensional grid pattern can be projected onto the web and captured using a camera. Any other suitable contact or non-contact technique could be used to identify the vertical position and/or tilt angle of a web.

The signal generator 120 and signal receiver 122 include any suitable structures for generating and receiving signals used in distance/tilt measurements. In some embodiments, the signal generator 120 includes one or more illumination sources, such as one or more light emitting diodes (LEDs), pulsed laser diodes, laser diode arrays, or other light source(s) configured to generate illumination for a tissue web. Also, in some embodiments, the signal receiver 122 includes one or more imaging devices, such as a CMOS, CCD, or other digital camera configured to capture digital images of a tissue web. Each processing device 124 includes any suitable processing or computing device, such as a microprocessor, microcontroller, digital signal processor, field programmable gate array, application specific integrated circuit, or discrete logic devices. Each memory 126 includes any suitable storage and retrieval device, such as a random access memory (RAM) or Flash or other read-only memory (ROM). Each interface 128 includes any suitable structure facilitating communication over a connection or network, such as a wired interface (like an Ethernet interface) or a wireless interface (like a radio frequency transceiver).

In particular embodiments, the functionality for measuring the stretch property of a tissue web can be incorporated into a FOTOSURF surface topography sensor available from HONEYWELL INTERNATIONAL INC. For example, software or firmware instructions for performing the techniques described in this patent document could be loaded onto at least one memory device in the FOTOSURF sensor and executed. The modified FOTOSURF sensor could then be used with the appropriate orientation and possibly backing to measure the stretch property of a tissue web. Structured light and a camera can be used in the modified FOTOSURF sensor to, for example, support laser triangulation at three points or other distance/tilt measurements.

Measurements from the scanner 118 can be used in any suitable manner, such as to optimize or control the tissue web manufacturing process. For example, the scanner 118 can provide measurements to at least one controller 130, which can adjust the manufacturing or other process(es) based on the measurements. As a particular example, the controller(s) 130 could adjust the operation of the headbox 102, Yankee dryer 110, creping doctor 112, reel 114, and/or spray boom 116 based on the measurements.

Each controller 130 includes any suitable structure for controlling at least part of a process. For example, each controller 130 could include at least one processing device 132, at least one memory 134, and at least one interface 136. The processing device(s) 132 can execute control logic for adjusting a manufacturing or other process. The memory or memories 134 can store the control logic or other control functionality and any related data. The interface(s) 136 can support communications with other devices, such as the scanner 118 and any actuators for adjusting the manufacturing process.

Each processing device 132 includes any suitable processing or computing device, such as a microprocessor, microcontroller, digital signal processor, field programmable gate array, application specific integrated circuit, or discrete logic devices. Each memory 134 includes any suitable storage and retrieval device, such as a RAM or ROM. Each interface 136 includes any suitable structure facilitating communication over a connection or network, such as a wired interface (like an Ethernet interface) or a wireless interface (like a radio frequency transceiver).

Among other things, the use of one or more online sensors for measuring the stretch property of a tissue web can allow the stretch property to be controlled during manufacturing or processing. This can help to increase web quality and reduce production losses associated with the manufacturing or processing. Moreover, this can be done without requiring destructive testing of the web. In addition, "converting" refers to a process where a web is converted into a desired final product. Controlling a web's stretch property can help to increase the efficiency of a subsequent converting process, such as by helping to reduce web breaks or manual interventions during the converting process.

Although FIG. 1 illustrates one example of a system 100 for identifying stretch measurements of a tissue web, various changes may be made to FIG. 1. For example, the functional division shown in FIG. 1 is for illustration only. Various components in FIG. 1 could be combined, further subdivided, or omitted and additional components could be added according to particular needs. As a particular example, the scanner 118 could output data (such as images or position/tilt measurements) so that an external device or system (such as a controller 130) can estimate the stretch property of a web. Also, FIG. 1 illustrates a simplified example of one type of system that can be used to manufacture creped tissue paper. Various details are omitted in this simplified example since they are not necessary for an understanding of this disclosure. In addition, the techniques described in this patent document for measuring the stretch property of a tissue web could be used with any suitable tissue web (regardless of whether the web is creped) and with any suitable system for manufacturing or processing a tissue web.

FIGS. 2 through 6 illustrate example devices for supporting stretch measurements of tissue webs according to this disclosure. For ease of explanation, these devices are described as being used as part of the scanner 118 in the system 100 of FIG. 1. However, these devices could be used as part of any suitable sensing device and in any suitable system.

As described below, sensors can be used to capture one or two types of measurements of a web of material. One measurement involves the vertical position (often referred to as the "z position") of a web of material after the Yankee cylinder 110 or other location where the web is not supported (meaning in an open draw). Another measurement involves the tilt angle of a web of material in an open draw, such as the tilt angle in the machine direction or the cross direction. Each type of measurement could be captured at one location of the web or at multiple locations of the web. Measurements at multiple locations of the web could be captured using one or more scanning devices that move or using stationary devices at fixed locations. The vertical position and/or tilt angle of a specific web of material can be captured and used in one or more mathematical formulas, correlated with known stretch values of other webs, or otherwise used to estimate the stretch property of the specific web.

Figure 2:
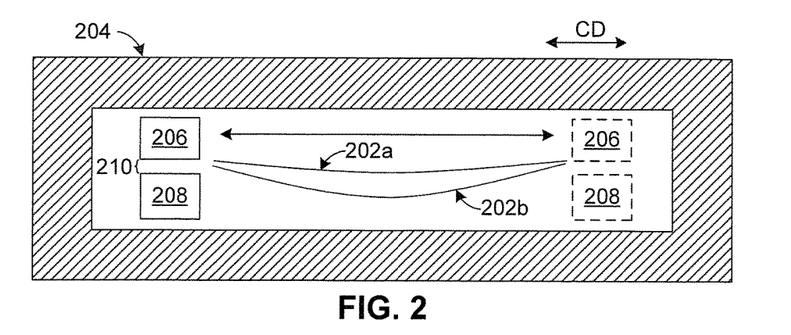
FIGS. 2 through 6 illustrate example devices for supporting stretch measurements of tissue webs according to this disclosure.

As shown in FIG. 2, a web of material can occupy various positions, such as positions 202a and 202b, within a beam 204. The position of the web can vary based on, among other factors, the stretch property of the web. The web of material passes through an opening within the beam 204, and one or more scanning heads 206-208 move back and forth along the beam 204. In this example, the scanning heads 206-208 can move back and forth across the entire width of the web, although this need not be the case. Note that while the beam 204 is shown as being rectangular here, the beam 204 could have any other suitable shape.

The scanning heads 206-208 operate to measure the web's vertical position and/or tilt angle. For example, each scanning head 206-208 could measure the web's distance from that scanning head or measure the web's tilt angle with respect to a known direction. In some embodiments, the scanning heads 206-208 move independently, and each scanning head 206-208 captures vertical position and/or tilt angle measurements at various locations. In other embodiments, the scanning heads 206-208 move together, and the scanning heads 206-208 operate to measure the web's vertical position and/or tilt angle within a measurement gap 210 (the space between the scanning heads 206-208).

Webs having higher stretch values would sag less and are therefore more likely to have a higher vertical position (such as position 202a) and a lower tilt angle in the frame 204. In contrast, webs having lower stretch values would sag more and are therefore more likely to have a lower vertical position (such as position 202b) and a higher tilt angle in the frame 204. Therefore, the vertical position and/or tilt angle of a specified web can be measured and used to estimate the current stretch property of the specified web.

Note that in FIG. 2, if the web of material sags below the measurement gap 210, the lower scanning head 208 could contact the web during movement of the scanning head 208. Similarly, if the web curls or is otherwise displaced above the measurement gap 210 (such as at the edges of the web), the upper scanning head 206 could contact the web during movement of the scanning head 206.

There are various ways in which potential contact with a web by a scanning head can be dealt with in order to effectively estimate the stretch property of the web. For example, in some embodiments, the web is allowed to contact the upper or lower scanning head 206 or 208, and the position of the web is assumed to be the top or bottom of the measurement gap 210, respectively. In one approach, the average position of the web across the entire width of the web could be calculated and used to estimate the stretch property of the web. Webs that sag more will have a maximum distance from the scanning head 206 and a minimum distance from the scanning head 208 over larger portions of their width compared to webs that sag less. The average distance from the scanning head 206 or the scanning head 208 can therefore still be used to estimate the stretch property of the current web being measured, even when contact with the web occurs.

Figure 3:
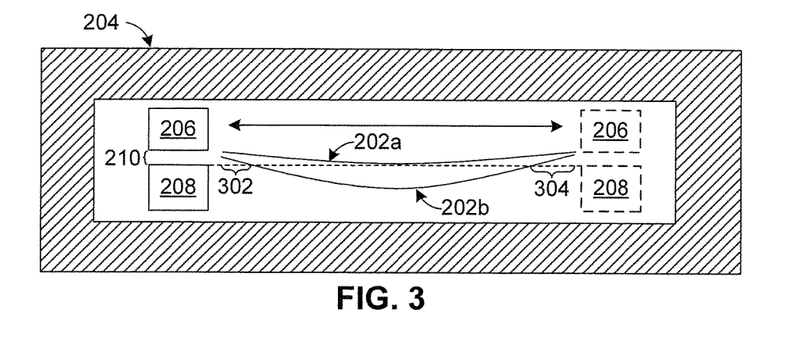

In other embodiments, only areas of a web not affected by contact with a scanning head may be utilized to estimate the stretch property of the web. An example of this is shown in FIG. 3, where measurements of a web may be confined to two areas 302-304 at edges of the web. Different scanning heads could be used at opposite edges of the web to capture vertical position and/or tilt angle measurements of the web in these two areas 302-304. Even in these limited areas 302-304, the vertical position and/or tilt angle of the web can be determined and used to estimate the stretch property of the web.

Note that the size(s) of the areas 302-304 could vary depending on current process conditions. For instance, the areas 302-304 could be larger when the web is in the higher position 202a since there is little or no contact with the scanning heads 206-208 when the web is in that position. The areas 302-304 could be identified in any suitable manner, such as by using one scanning head (such as scanning head 206) to measure vertical distance to the web and comparing that vertical distance to the known size of the measurement gap 210. The other scanning head (scanning head 208) could then be moved within a limited area based on knowledge of where the web sags below the measurement gap.

In still other embodiments, one or more scanning heads 206-208 could be positioned in locations where contact with the web is unlikely. For example, the scanning head 208 could be positioned below the maximum expected sagging position of the web.

Each scanning head 206-208 shown here could include any number of sensors. For example, each scanning head 206-208 could only include one or more sensors for measuring vertical position and/or tilt angle of a web of material. As another example, each scanning head 206-208 could include one or more sensors for measuring vertical position and/or tilt angle of a web of material, plus components for measuring one or more other characteristics of the web of material. Other sensors that could be used include sensors for measuring the caliper, anisotropy, basis weight, color, gloss, sheen, haze, or surface features (such as roughness, topography, or orientation distributions of surface features) of a web. As a particular example, a scanning head 206-208 could use captured images of a web to estimate both (i) the vertical position and/or tilt angle of the web and (ii) the crepe structure of the web (such as folds per unit length or macro crepe of the web). However, any suitable technique(s) could be used to measure vertical position and/or tilt angle of a web of material, including those mentioned above.

Figure 4:
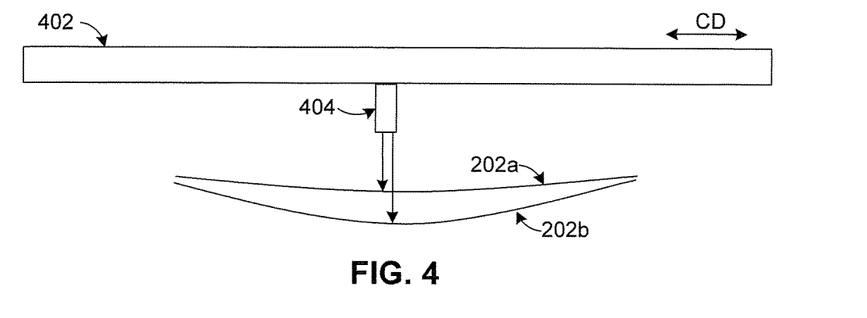

While moving sensors are shown in FIGS. 2 and 3, stationary sensors could also be used. For example, as shown in FIG. 4, a web of material could be passed under a frame 402 that supports a single sensor 404, and the sensor 404 could measure at least the vertical position and/or tilt angle of the web using any suitable technique. While shown as residing above the web, the sensor 404 could also reside below the web. In some embodiments, the sensor 404 could be located at or near an expected center of the web in the cross direction, which could represent the area where the maximum amount of sagging may occur in the web.

Figure 5:
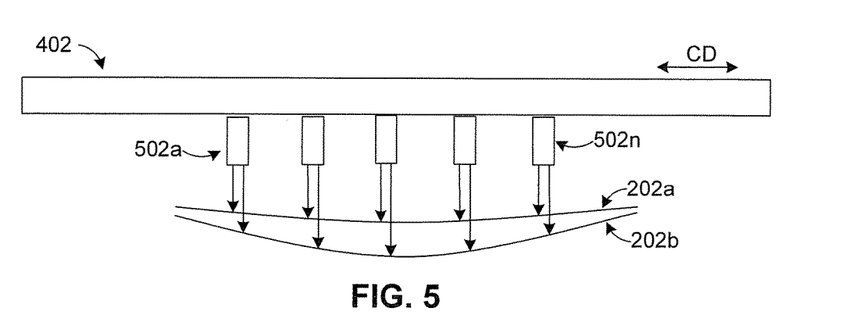

As shown in FIG. 5, multiple stationary sensors 502a-502n could also be distributed across at least part of the width of a web of material. These sensors 502a-502n measure at least the vertical position and/or tilt angle of the web at different locations in the cross direction. While shown here as extending across the width of the web, the sensors 502a-502n could also be arranged in the machine direction or in any arbitrary direction.

Figure 6:
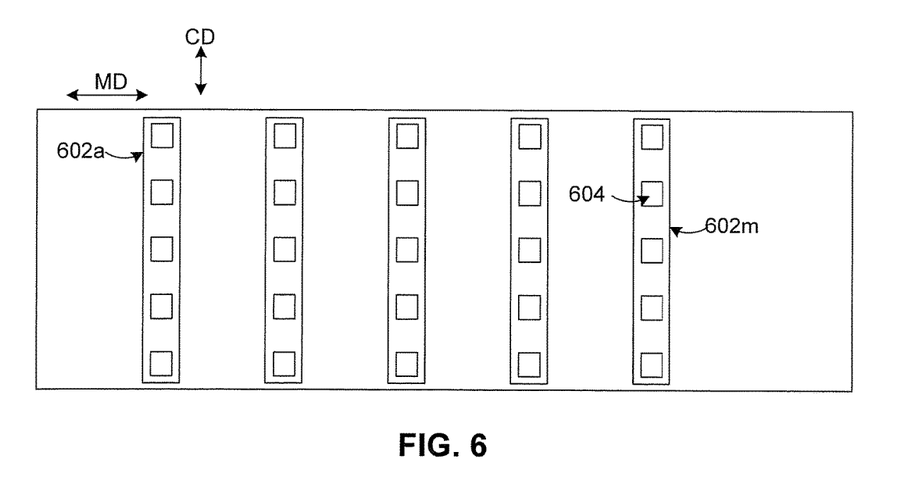

Sensors could also be used at any number of positions along the length of the web. As shown in FIG. 6, multiple sets 602a-602m of stationary sensors 604 could be used to identify at least the vertical position and/or tilt angle of a web at multiple locations in the machine direction. The sensors 604 in these sets 602a-602m could be aligned in the machine direction and/or offset in the machine direction.

In general, any fixed/movable sensor or combination of fixed/movable sensors could be used to capture vertical position and/or tilt angle measurements of a web. These measurements could occur at any suitable location(s) of a web. The measurements can then be used in one or more mathematical formulas, correlated to vertical position and/or tilt angle measurements for webs with known stretch values (such as known laboratory values), otherwise used to estimate the stretch property of the current web being measured.

One or multiple vertical position and/or tilt angle measurements of a web could be used to estimate the stretch property of the web. If multiple measurements are used, one or more measurements could be selected, the measurements could be combined, or one or more statistical values of the measurements could be calculated and then used to estimate the stretch property of the current web being measured. For example, the average or standard deviation of the measurements could be calculated, or the lowest hanging point of the web could be identified. As another example, coefficients of a polynomial fit to the measurements could be identified, or a Kurtosis value associated with a shape of the web's profile could be calculated. As yet another example, the frequency of variations in the position and/or tilt angle could be identified, such as a frequency expressed in time (Hz) and/or space (1/m). Any of these parameters could then be used to estimate the stretch property of the current web being measured. In general, any parameter or parameters defining a profile form or shape of a web could be identified and then used to identify the stretch property of the current web.

Once vertical position and/or tilt angle measurements of a web have been captured (such as by using one or more of the approaches described above), the measurements are used to estimate the stretch property of the web. For example, one or more mathematical formulas could use the measurements to determine the stretch property of the web. The mathematical formula(s) could be defined using position and/or tilt angle measurements captured for webs with known stretch values (such as laboratory measurements of those webs' stretch values). As another example, the measurements can be correlated against measurements associated with known stretch values, one or more known stretch values can be selected (such as by selecting those known stretch values with measurements closest to the current measurements), and the selected known stretch values can be used to estimate the stretch property of the web.

In some embodiments, known stretch values are identified using "training" webs. One or more sensors capture vertical position and/or tilt angle measurements of the training webs during manufacture or processing of the training webs, and laboratory values of the training webs' stretch property are identified. The laboratory values could be identified in any suitable manner, such as in accordance with the ISO 12625-4:2005 specification. These laboratory values represent known stretch values of the training webs. The training webs could vary in grade or other characteristics. Once an adequate number of known stretch values associated with training webs are identified, mathematical formulas can be identified that associate the measured position and/or tilt angle measurements with the known stretch values, and vertical position and/or tilt angle measurements for an additional web can be captured and plugged into the mathematical formulas. Alternatively, once an adequate number of known stretch values associated with training webs are identified, position and/or tilt angle measurements for an additional web can be captured, and the known stretch value for at least one training web can be selected and used to estimate the stretch property of the additional web.

Note that various types of pre-processing could occur to position and/or tilt angle measurements in order to generate pre-processed measurements that are used to estimate the stretch property of a web. For example, position measurements can be interpolated, decimated, differentiated, integrated, convoluted, filtered, and/or otherwise mathematically processed to generate a position profile or a position field. Similar operations could occur using tilt angle measurements to generate a tilt angle profile or a tilt angle field.

As noted above, single-point or multi-point measurements could be used to estimate the stretch property of a web. For example, if sensor measurements are captured at a single location, measurements captured at that location can be used in one or more mathematical formulas or compared to sensor measurements taken for the training webs. If a position and/or tilt angle profile is generated using sensors at multiple locations, a parameter of the profile (such as the profile's average) could be computed or a polynomial could be fit to the profile's shape and used to estimate the stretch property. However it is done, one or more position and/or tilt angle measurements can be used to estimate the stretch property of the current web.

It is further possible to calibrate the stretch estimation depending on various process parameters. For example, the laboratory measurements used to estimate the stretch property of a web could vary based on the grade of tissue paper currently being manufactured or processed. As a particular example, different sets of training webs could be used to collect the laboratory measurements (where the different sets have training webs of different grades), and mathematical formulas or laboratory measurements associated with one set could be selected based on the current grade of tissue paper being manufactured or processed. Similarly, different laboratory measurements could be used to estimate the stretch property of a web based on the crepe percentage currently being used. As a particular example, different sets of training webs could be used to collect the laboratory measurements (where the different sets experienced different crepe percentages), and mathematical formulas or laboratory measurements associated with one set could be selected based on the current crepe percentage being used. The crepe percentage is a grade-dependent parameter that, in some embodiments, can be expressed as:

$$((RS_{YD}-RS_{R/D})/RS_{YD})*100 \quad (1)$$

where $RS_{YD}$ denotes the rotational speed of the Yankee dryer 110 and $RS_{R/D}$ denotes the rotational speed of the reel or drum 114. In addition, different laboratory measurements could be used to estimate the stretch property of a web based on the crepe structure (such as folds per unit length or macro crepe) of the current web being manufactured or processed. Example techniques for identifying the folds per unit length and macro crepe of a web are provided below. Any of these factors or other process parameters or any combination of these factors or other process parameters could be incorporated into the estimation of stretch for a web, such as via selection of different mathematical equations or laboratory measurements or the inclusion of various correction factors into calculations.

To summarize the above, the vertical position and/or tilt angle of a current web of material can be captured at one or more locations. The measurements are then used in one or more mathematical formulas, correlated to measurements associated with known stretch values (such as laboratory measurements of training webs), or otherwise used to estimate the stretch value of the current web of material. A wide variety of techniques could be used to pre-process the measurements of the current web and/or to correlate the measurements of the current web with the measurements associated with the known stretch values.

Although FIGS. 2 through 6 illustrate examples of devices for supporting stretch measurements of tissue webs, various changes may be made to FIGS. 2 through 6. For example, any number of sensors could be used to capture measurements of a web, and any combination of stationary and/or fixed sensors could be used. Also, the sensors could be used to capture only vertical position measurements, only tilt angle measurements, or a combination of position and tilt angle measurements. Depending on the circumstances, it may also be possible to estimate tilt angle measurements using only position measurements of a web, in which case position measurements can be captured and tilt angle measurements inferred from the position measurements.

Figure 7:
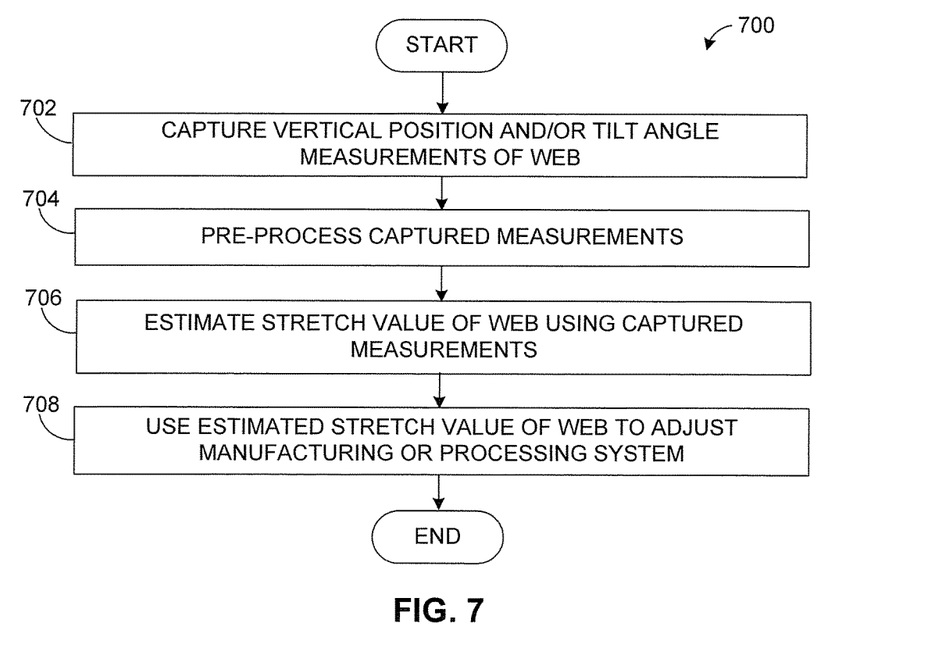
FIG. 7 illustrates an example method for stretch measurements of tissue webs according to this disclosure.

FIG. 7 illustrates an example method 700 for stretch measurements of tissue webs according to this disclosure. For ease of explanation, the method 700 is described as being performed by the scanner 118 in the system 100 of FIG. 1. However, the method 700 could be used by any suitable sensing device and in any suitable system.

As shown in FIG. 7, vertical position and/or tilt angle measurements of a web of material are captured at step 702.

This could include, for example, using the signal generator 120 and the signal receiver 122 to capture vertical position and/or tilt angle measurements of the web of material at one or multiple locations. Fixed and/or scanning sensors could be used to capture the measurements, and various techniques (including those described above) could be used to generate position readings or tilt angle readings.

Pre-processing of the captured sensor measurements can occur at step 704. This could include, for example, using the processing device 124 to pre-process the captured vertical position and/or tilt angle measurements. The pre-processing could involve various functions, such as interpolation, decimation, differentiation, integration, convolution, or filtering. Among other things, the pre-processing could be used to help reduce or remove variations in web positions or tilt angles caused by perturbations. However, pre-processing of the captured sensor measurements is optional.

A stretch value of the web is estimated using the captured measurements is (with or without pre-processing) at step 706. Depending on the implementation, factors such as product grade, crepe percentage, crepe structure, or other or additional factors could be used to calculate the stretch value of the web. This step could include, for example, the processing device 124 plugging the captured measurements into one or more mathematical formulas to identify a web stretch value. This could also include the processing device 124 comparing the captured measurements with prior measurements obtained for various training webs, identifying the prior measurement(s) closest to the captured measurements, selecting laboratory stretch values associated with the closest prior measurement(s), and identifying an estimated stretch value for the web using the identified laboratory stretch values.

Note that the analysis in step 706 could occur using any of the approaches described above. For example, the average, standard deviation, lowest hanging point, coefficients of a polynomial fit, Kurtosis value, frequency of variations, or any other or additional parameter(s) of one or more position and/or tilt measurements could be used. Also, any suitable technique could be used to generate mathematical formulas or to correlate one or more captured measurements with one or more prior measurements associated with known stretch values.

The estimated stretch value of the web can be used in any suitable manner. For example, as shown in FIG. 7, the estimated stretch value of the web can be used to adjust a manufacturing or processing system that is producing or processing the web of material in some manner at step 708. This could include, for example, the processing device 124 communicating the estimated stretch value of the web to a process controller 130 via an interface 128. The controller 130 could then alter the manufacturing or processing system in order to maintain the stretch property of the web at or near a desired setpoint or within a desired range of values. If the functionality of the processing device(s) 124 is incorporated into a process controller 130, the estimated stretch value of the web could be used directly.

Although FIG. 7 illustrates one example of a method 700 for stretch measurements of tissue webs, various changes may be made to FIG. 7. For example, while shown as a series of steps, various steps in FIG. 7 could overlap, occur in parallel, or occur any number of times.

Figure 8:
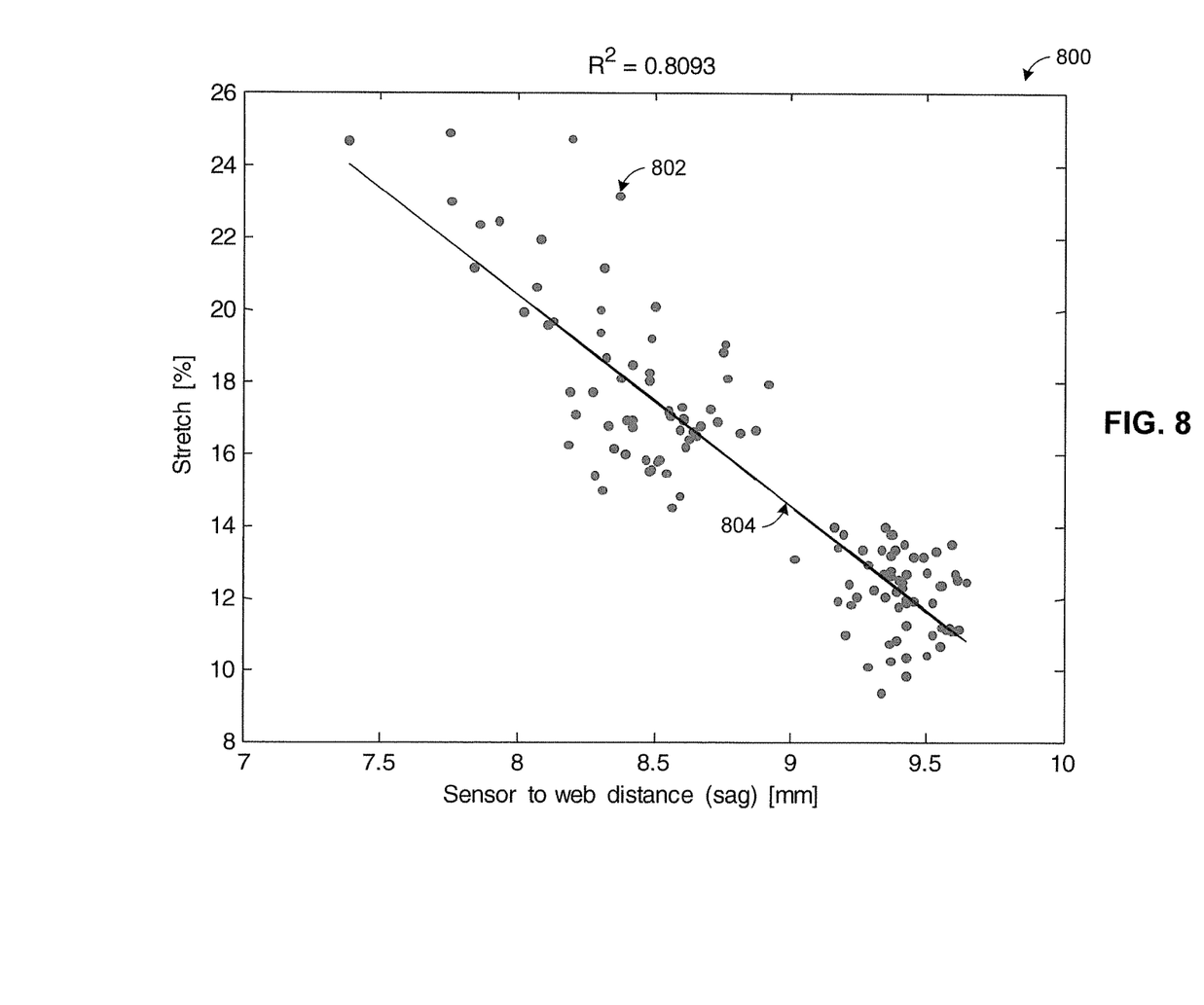
FIG. 8 illustrates an example plot showing a mathematical correlation between sensor measurements and web stretch values according to this disclosure.

FIG. 8 illustrates an example plot 800 showing a mathematical correlation between sensor measurements and web stretch values according to this disclosure. The plot 800 here includes various points 802, which identify vertical position measurements and their associated known stretch values. These points 802 can be identified for a specific system by manufacturing or processing various training webs in the system, capturing the vertical position measurements using one or more sensors, and identifying laboratory stretch values for the training webs.

A line 804 represents a mathematical formula that correlates the vertical position measurements with the known laboratory stretch values. The line 804 could be straight or curved. The mathematical formula could be identified in any suitable manner, such as via interpolation, extrapolation, or curve fitting. Once the mathematical formula is known, the mathematical formula can be provided to a sensor or other device and used to estimate the stretch property of additional webs manufactured in the system.

Although FIG. 8 illustrates one example of a plot 800 showing a mathematical correlation between sensor measurements and web stretch values, various changes may be made to FIG. 8. For instance, the specific points and line shown here are examples only and relate to one specific system tested.

Figure 9:
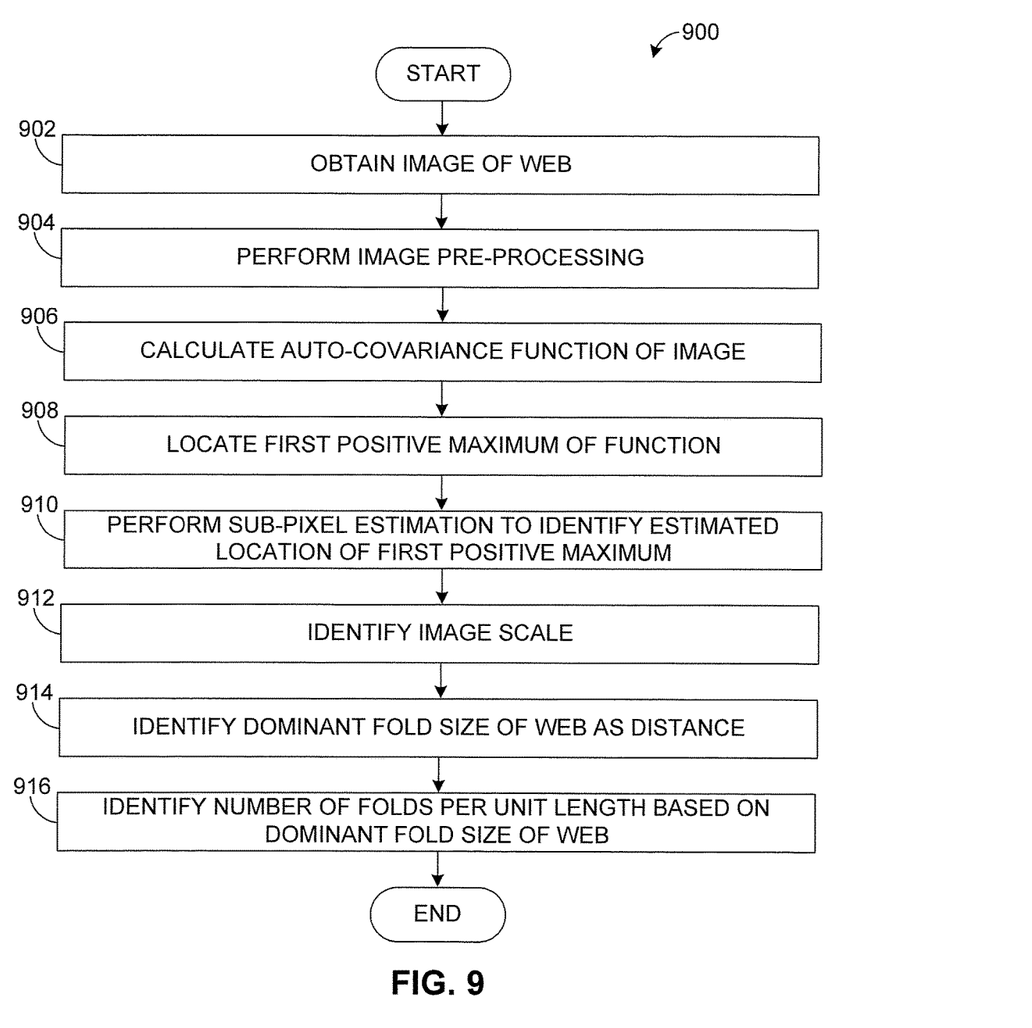
Figure 10A:
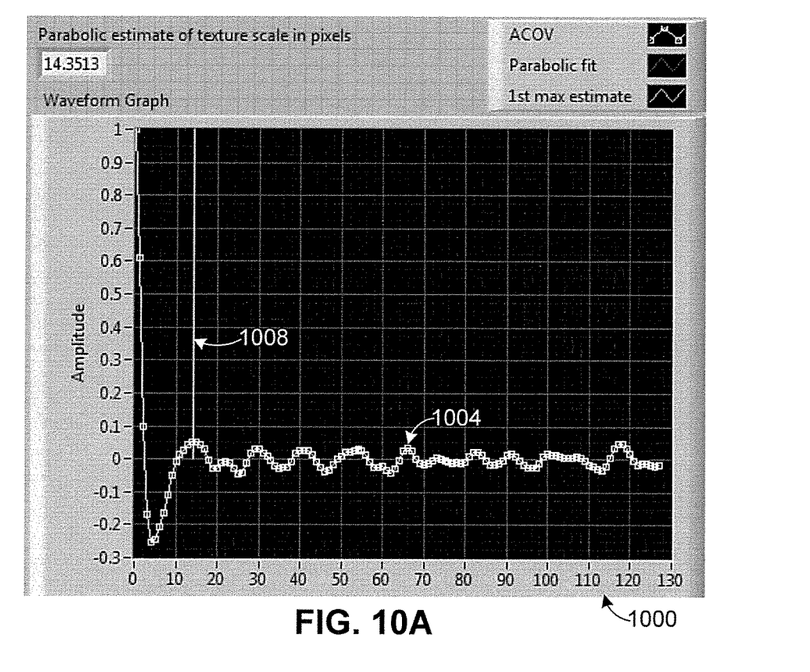
Figure 10B:
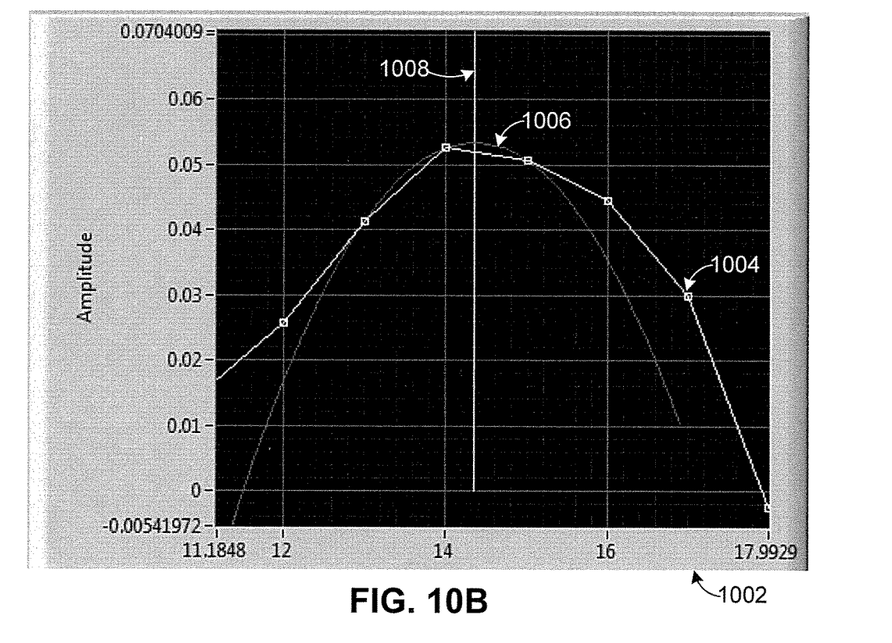

FIGS. 9 through 10B illustrate example techniques for identifying crepe structures of tissue webs according to this disclosure. The folds per unit length identifies the number of folds of a dominant fold size that fit within some unit length of a web (such as within a one-inch wide area of the web). The macro crepe value identifies the variance of reflected light (graylevel) related to the dominant fold size of the web.

FIG. 9 illustrates an example method 900 for identifying the dominant fold size of a web according to this disclosure. The method 900 could, for example, be used to identify the dominant fold size of a web so that the number of folds per unit length and/or macro crepe values of a web of material can be identified. As noted above, these crepe structure values could be used to (among other things) select appropriate mathematical formulas or known stretch values in order to estimate the stretch property of the web. Note, however, that other approaches for identifying the dominant fold size of a web could be used.

As shown in FIG. 9, an image of a web is obtained at step 902. This could include, for example, the processing device 124 obtaining an image of a web from the signal receiver 122. The image could represent a one-dimensional or multi-dimensional image. In some embodiments, the image can be captured using any suitable illumination, such as annular illumination, oblique illumination, or any other illumination. The image can also be captured at any suitable angle, such as substantially normal to the web. In particular embodiments, the image obtained at step 902 could be the same image obtained during the method 700 to estimate the vertical position and/or tilt angle of the web.

Image pre-processing occurs at step 904. This could include, for example, the processing device 124 digitally correcting the image for any unevenness in the illumination of the web. This could also include the processing device 124 digitally correcting the image for any tilting of the imaging device or the web. Any other or additional optical, geometrical, or statistical corrections could be performed, such as to compensate for optical aberrations, vignetting, depth of focus, and temperature-dependent noise.

An auto-covariance function of the image is identified at step 906. This could include, for example, the processing device 124 generating a discrete auto-covariance function using the pre-processed image data. A discrete auto-covariance function of an image can be determined in various domains, such as the spatial domain or the frequency domain (like after a fast Fourier transform or other transform). A discrete auto-covariance function can be generated to represent the similarity of or relationship between the gray level of adjacent pixels, pixels that are separated by one pixel, pixels that are separated by two pixels, and so on in a particular direction. The direction could represent a row or column of a Cartesian coordinate system or a radial direction of a polar coordinate system. The resulting functions can then be averaged, such as for all rows/columns or in all radial directions, to create a final discrete auto-covariance function. The final auto-covariance function can be defined using a series of discrete points, such as where the discrete points are defined as values between −1 and +1 (inclusive) for whole numbers of pixels. Note that the phrase "auto-covariance" can be used interchangeably with "auto-correlation" in many fields. In some embodiments, the auto-covariance function represents an auto-covariance function normalized by mean and variance, which is also called an "auto-correlation coefficient."

In particular embodiments, for one-dimensional discrete data, an auto-covariance function (auto-correlation coefficient) in the spatial domain can be expressed as:

$$R(\tau) = \frac{E[(X_t - \mu)(X_{t+\tau} - \mu)]}{\sigma^2} \quad (2)$$

where E denotes an expected value operator, $X_t$ denotes the data value at index (time) t, $\tau$ denotes the distance (time lag) between data points, $\mu$ denotes the mean value of the data points, and $\sigma^2$ denotes the variance of the data points. In the above equation, a second-order stationary process is assumed.

In other particular embodiments, for two-dimensional discrete data, the auto-covariance function (auto-correlation coefficient) in the spatial domain for the $j^{th}$ row of a two-dimensional gray level image $g_{i,j}$ as a function of pixel distance k can be expressed as:

$$R_j(k) = \frac{1}{(n-k)\sigma^2} \sum_{i=1}^{n-k} (g_{i,j} - \mu)(g_{i+k,j} - \mu) \quad (3)$$

where k is less than n, $\mu$ denotes the mean gray level of the image, and $\sigma^2$ denotes the variance in gray level of the image. The average auto-covariance function for the image rows can then be calculated as:

$$\overline{R(k)} = \frac{1}{m} \sum_{i=1}^{m} R_i(k) \quad (4)$$

Note that the mean auto-covariance function (auto-correlation coefficient) as a function pixel distance is not limited to use with rows of pixel data. Rather, it can be calculated with any dimension or direction in an image.

An auto-covariance function in the frequency domain could be computed using the Wiener-Khinchin theorem in a one-dimensional case as:

$$G(f) = FFT[X_t - \mu] \quad (5)$$

$$S(f) = G(f)G^*(f) \quad (6)$$

$$R(\tau) = IFFT[S(f)] \quad (7)$$

Here, FFT[ ] denotes a Fast Fourier Transform, IFFT[ ] denotes an Inverse Fast Fourier Transform, and G* denotes the complex conjugate of G. This technique can also be used in each row, column, or other direction of a two-dimensional image. An average of the auto-covariance functions of multiple lines can be computed to obtain the average auto-covariance function of an image efficiently. This technique can be applied to any discrete data with any dimension or direction.

A position of the first positive local maximum of the auto-covariance function (when moving away from the origin) is identified at step 908. This could include, for example, the processing device 124 identifying a positive number of whole pixels associated with the first positive local maximum of the auto-covariance function. This position can be denoted $x_p$.

Sub-pixel estimation is performed to identify a more accurate position of the first positive local maximum of the auto-covariance function at step 910. This could include, for example, the processing device 124 performing a curve-fitting algorithm using the discrete points at and around the $x_p$ position to identify a fitted polynomial. As a particular example, the processing device 124 could fit a second-order polynomial to the discrete point at the $x_p$ position and the discrete points closest to the $x_p$ position. The maximum value of the fitted polynomial is identified, and the position of that maximum value is used as the sub-pixel estimate of the auto-covariance function. The sub-pixel estimate represents the dominant fold size contained in the obtained image expressed as a number of pixels (both whole and fractional pixels).

The dominant fold size expressed as a number of pixels could be converted into a measure of distance. To do this, an image scale is identified at step 912. This could include, for example, the processing device 124 determining a real-world distance corresponding to each pixel in the obtained image. The real-world distance can be based on various factors, such as the distance of the imaging device from the web, the focal length and zoom of the imaging device when the image was captured, and the chip or sensor type of the imaging device. The real-world distance can also be determined using a calibration target of a known size. The dominant fold size in terms of distance is identified at step 914. This could include, for example, the processing device 124 multiplying the sub-pixel estimate identified earlier (which represents the dominant fold size expressed as a number of pixels) and the image scale (which represents the distance each pixel represents). The resulting value expresses the dominant fold size as a measure of length.

The dominant fold size is used to estimate the number of folds per unit length of the web at step 916. This could include, for example, the processing device 124 dividing some unit length (such as one inch) by the dominant fold size expressed as a measure of length. The resulting value denotes a count of the number of folds having the dominant fold size that can fit within the unit length.

Although FIG. 9 illustrates one example of a method 900 for identifying the dominant fold size of a web, various changes may be made to FIG. 9. For example, while shown as a series of steps, various steps in FIG. 9 could overlap, occur in parallel, occur in a different order, or occur multiple times. As a particular example, it is possible to have both pre-processing of the image and post-calculation adjustment to the dominant fold size.

FIGS. 10A and 10B illustrate an example of identifying the dominant fold size of a web according to this disclosure. In FIGS. 10A and 10B, two graphs 1000-1002 could be generated using an image of a creped tissue paper. In FIG. 10A, the graph 1000 includes various discrete points 1004, which represent the values of a discrete auto-covariance function. As can be seen here, the first positive local maximum that is encountered when moving away from the origin occurs at a pixel distance of 14. The processing device 124 then fits a polynomial curve 1006 against the point 1004 at that pixel distance and its neighboring points 1004. The maximum value of the polynomial curve 1006 is denoted with a line 1008, which also represents the dominant fold size expressed in terms of pixels. In this example, the dominant fold size represents 14.3513 pixels. By calculating the distance per pixel, the dominant fold size can be expressed as a length.

Although FIGS. 10A and 10B illustrate one example of identifying the dominant fold size of a web, various changes may be made to FIGS. 10A and 10B. For instance, this example is for illustration only and does not limit the system 100 of FIG. 1 or the methods 700, 800 to any particular implementation.

In some embodiments, the macro crepe value for a web can be calculated by integrating a one-sided power spectral density $P(v)$ of a graylevel signal over a band between frequencies $v_1$ and $v_2$ that cover the dominant fold frequency (denoted $\omega$). The dominant fold frequency $\omega$ denotes the number of dominant folds per unit length. The macro crepe value can therefore be expressed as follows:

$$\text{Macro Crepe} = \sigma_r^2(v_1, v_2) = \int_{v_1}^{v_2} P(v)dv \quad (8)$$

where $\sigma_r$ denotes the standard deviation of diffusely-reflected light from the web. For $v_1$ and $v_2$, it holds that $\omega \in [v_1, v_2]$. Frequencies $v_1$ and $v_2$ can be constants that satisfy this condition, or $v_1$ and $v_2$ could be dynamically dependent on the dominant fold frequency $\omega$. For computational efficiency, the power spectral density $P(v)$ can be extracted as a side product from an FFT-based auto-covariance computation (described above with respect to FIG. 9). An average of power spectral density of lines can be computed to obtain the average power spectral density of an image efficiently. This method can be applied for any discrete data with any dimension or direction.

The number of folds per unit length and/or the macro crepe value of a web can be used to help identify the crepe structure of the web. That crepe structure can be incorporated into the estimation of the stretch property of the web. For example, different mathematical formulas or known stretch values could be identified for training webs having different crepe structures, and appropriate mathematical formulas or known stretch values could be selected based on the crepe structure of the current web being scanned. As another example, a correction factor based on the crepe structure of the current web could be used during the calculation of the current web's stretch property. The crepe structure of a web could be used in any other suitable manner to identify the stretch property of that web.

Additional details regarding the identification of crepe structure are provided in U.S. patent application Ser. No. 14/225,703, which is hereby incorporated by reference in its entirety. Note, however, that any other suitable technique(s) could be employed to measure the crepe structure of a tissue web.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc, a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
   using at least one processing device:
      obtaining at least one of position measurements and tilt angle measurements associated with a tissue web, the obtained measurements representing a sag of the tissue web in an open draw where the tissue web sags under its own weight; and
      identifying a stretch measurement associated with the tissue web using the obtained measurements, the stretch measurement representing a measure of an amount that the tissue web is able to potentially stretch before breaking.

2. The method of claim 1, wherein identifying the stretch measurement comprises:
   using one or more mathematical formulas to calculate the stretch measurement associated with the tissue web using the obtained measurements.

3. The method of claim 2, wherein the one or more mathematical formulas are defined using laboratory stretch values of multiple training webs.

4. The method of claim 3, wherein:
different mathematical formulas are associated with training webs having different characteristics; and
the method further comprises selecting at least one of the mathematical foil futas based on one or more characteristics of the tissue web.

5. The method of claim 4, wherein the one or more characteristics of the tissue web comprise at least one of: a grade of the tissue web, a crepe percentage associated with the tissue web, and a crepe structure of the tissue web.

6. The method of claim 1, wherein identifying the stretch measurement comprises:
comparing the obtained measurements to measurements associated with known stretch values;
selecting at least one of the known stretch values based on the comparison; and
identifying the stretch measurement using the selected at least one known stretch value.

7. The method of claim 1, wherein obtaining at least one of the position measurements and the tilt angle measurements comprises capturing the measurements using at least one sensor.

8. The method of claim 7, wherein:
the at least one sensor comprises at least one movable sensor; and
capturing the measurements comprises confining the at least one movable sensor to one or more locations where the at least one movable sensor does not contact the tissue web.

9. The method of claim 7, wherein:
the at least one sensor comprises multiple sensors; and
identifying the stretch measurement comprises identifying one or more parameters defining a profile form or shape of the tissue web.

10. The method of claim 1, wherein the position measurements identify distances of the tissue web from a known location.

11. The method of claim 1, wherein the tilt angle measurements identify a tilt of the tissue web with respect to a known direction.

12. A non-transitory computer readable medium containing a computer program, the computer program comprising, computer readable program code that when executed causes at least one processing device to:
obtain at least one of position measurements and tilt angle measurements associated with a tissue web, the obtained measurements representing a sag of the tissue web in an open draw where the tissue web sags under its own weight; and
identify a stretch measurement associated with the tissue web using the obtained measurements, the stretch measurement representing a measure of an amount that the tissue web is able to potentially stretch before breaking.

13. The non-transitory computer readable medium of claim 12, wherein the computer readable program code that when executed causes the at least one processing device to identify the stretch measurement comprises:
computer readable program code that when executed causes the at least one processing device to use one or more mathematical formulas to calculate the stretch measurement associated with the tissue web using the obtained measurements.

14. The non-transitory computer readable medium of claim 13, wherein:
the one or more mathematical formulas are defined using laboratory stretch values of multiple training webs;
different mathematical formulas are associated with training webs having different characteristics; and
the computer program further comprises computer readable program code that when executed causes the at least one processing device to select at least one of the mathematical formulas based on one or more characteristics of the tissue web.

15. The non-transitory computer readable medium of claim 14, wherein the one or more characteristics of the tissue web comprise at least one of: a grade of the tissue web, a crepe percentage associated with the tissue web, and a crepe structure of the tissue web.

16. The non-transitory computer readable medium of claim 12, wherein the computer readable program code that when executed causes the at least one processing device to identify the stretch measurement comprises computer readable program code that when executed causes the at least one processing device to:
compare the obtained measurements to measurements associated with known stretch values;
select at least one of the known stretch values based on the comparison; and
identify the stretch measurement using the selected at least one known stretch value.

17. The non-transitory computer readable medium of claim 12, wherein the computer readable program code that when executed causes the at least one processing device to obtain at least one of the position measurements and the tilt angle measurements comprises:
computer readable program code that when executed causes the at least one processing device to obtain the measurements from at least one sensor.

18. The non-transitory computer readable medium of claim 17, wherein:
the at least one sensor comprises at least one movable sensor; and
the computer program further comprises computer readable program code that when executed causes the at least one processing device to confine the at least one movable sensor to one or more locations where the at least one movable sensor does not contact the tissue web.

19. The non-transitory computer readable medium of claim 17, wherein:
the at least one sensor comprises multiple sensors; and
the computer program further comprises computer readable program code that when executed causes the at least one processing device to identify one or more parameters defining a profile form or shape of the tissue web.

20. An apparatus comprising:
at least one memory configured to store obtained measurements comprising at least one of position measurements and tilt angle measurements associated with a tissue web, the obtained measurements representing a sag of the tissue web in an open draw where the tissue web sags under its own weight; and
at least one processing device configured to identify a stretch measurement associated with the tissue web using the obtained measurements, the stretch measurement representing a measure of an amount that the tissue web is able to potentially stretch before breaking.

21. The apparatus of claim 20, wherein the at least one processing device is configured to use one or more mathematical formulas to calculate the stretch measurement associated with the tissue web using the obtained measurements.

22. The apparatus of claim 20, wherein the at least one processing device is configured to:
  compare the obtained measurements to measurements associated with known stretch values;
  select at least one of the known stretch values based on the comparison; and
  identify the stretch measurement using the selected at least one known stretch value.

23. The apparatus of claim 20, further comprising:
at least one movable sensor configured to capture the measurements;
  wherein the at least one processing device is further configured to confine the at least one movable sensor to one or more locations where the at least one movable sensor does not contact the tissue web.

24. The apparatus of claim 20, further comprising:
multiple sensors configured to capture the measurements;
  wherein the at least one processing device is further configured to identify one or more parameters defining a profile form or shape of the tissue web.

\* \* \* \* \*